United States Patent
Yeritsyan

(10) Patent No.: US 10,449,179 B2
(45) Date of Patent: Oct. 22, 2019

(54) STABLE VETERINARY ANTHELMINTIC FORMULATIONS

(71) Applicant: DONAGHYS LIMITED, Christchurch (NZ)

(72) Inventor: Karen Yeritsyan, Dunedin (NZ)

(73) Assignee: Donaghys Limited, Christchurch (NZ)

( * ) Notice: Subject to any disclaimer, the term of this patent is extended or adjusted under 35 U.S.C. 154(b) by 0 days.

(21) Appl. No.: 15/274,346

(22) Filed: Sep. 23, 2016

(65) Prior Publication Data

US 2017/0007584 A1 Jan. 12, 2017

Related U.S. Application Data

(63) Continuation of application No. PCT/NZ2015/000018, filed on Mar. 24, 2015.

(30) Foreign Application Priority Data

Mar. 24, 2014 (NZ) ........................................ 622869

(51) Int. Cl.
| | | |
|---|---|---|
| *A61P 33/00* | (2006.01) | |
| *A61K 9/00* | (2006.01) | |
| *A61K 9/08* | (2006.01) | |
| *A01N 25/02* | (2006.01) | |
| *A01N 43/90* | (2006.01) | |
| *A01N 47/18* | (2006.01) | |
| *A61K 47/10* | (2017.01) | |
| *A61K 47/20* | (2006.01) | |
| *A61K 47/26* | (2006.01) | |
| *A61K 31/365* | (2006.01) | |
| *A61K 31/429* | (2006.01) | |
| *A61K 31/4184* | (2006.01) | |
| *A61K 31/7048* | (2006.01) | |

(52) U.S. Cl.
CPC ............ *A61K 31/429* (2013.01); *A01N 43/90* (2013.01); *A61K 9/0017* (2013.01); *A61K 9/08* (2013.01); *A61K 31/365* (2013.01); *A61K 31/4184* (2013.01); *A61K 31/7048* (2013.01); *A61K 47/10* (2013.01); *A61K 47/20* (2013.01); *A61K 47/26* (2013.01)

(58) Field of Classification Search
CPC ............ A61K 31/429; A61K 31/4184; A61K 31/7048; A61K 31/365; A61K 47/10; A61K 47/26; A61K 47/20; A61K 9/08; A61K 9/0017; A01N 43/90
See application file for complete search history.

(56) References Cited

U.S. PATENT DOCUMENTS

| | | | |
|---|---|---|---|
| 5,965,603 A | 10/1999 | Johnson et al. | |
| 2008/0249153 A1 | 10/2008 | Razzak | |

FOREIGN PATENT DOCUMENTS

| | | | | | |
|---|---|---|---|---|---|
| NZ | 248486 | A | | 7/1996 | |
| NZ | 336139 | A | * | 7/2002 | ............ A01N 25/02 |
| NZ | 336139 | A | | 7/2002 | |
| NZ | 515772 | A | | 12/2002 | |
| NZ | 535644 | A | | 5/2007 | |
| RU | 2367435 | C1 | | 9/2009 | |
| WO | 2004/089239 | A2 | | 10/2004 | |
| WO | 2008/072985 | A2 | | 6/2008 | |
| WO | 2011/161209 | A1 | | 12/2011 | |
| WO | 2013/043064 | A1 | | 3/2013 | |
| WO | WO-2013030702 | A2 | * | 3/2013 | ............ A61K 9/0019 |
| WO | WO-2013043064 | A1 | * | 3/2013 | ............... A61D 7/00 |

OTHER PUBLICATIONS

Kudo et al., Veterinary Parasitology, 2008, 151, p. 46-52. (Year: 2008).*
Certified copy of priority document NZ 622869 retrieved from WIPO, www.wipo.int, accessed online on Feb. 1, 2018. (Year: 2018).*
Coopers Animal Health, "Sheep Drenches: Effective internal parasite control in sheep", published on Aug. 31, 2007 as per Wayback Machine [online] [retrieved from the internet on Jun. 9, 2015] <URL:http://www.coopersanimalhealth.com.au/tt/sp/2910164402.pdf>.
International Search Report for International Patent Application No. PCT/NZ2015/000018, dated Jul. 29, 2015.
Written Opinion of the International Searching Authority for International Patent Application No. PCT/NZ2015/000018, dated Jul. 29, 2015.
International Preliminary Report on Patentability (Chapter II of the Patent Cooperation Treaty) for International Patent Application No. PCT/NZ2015/000018, dated Jul. 14, 2016.
Paul R. Klink et al., Formulation of Veterinary Dosage Forms, in 88 Drugs and the Pharmaceutical Sciences: Development and Formulation of Veterinary Dosage Forms 145, 212 (Gregory E. Hardee et al. eds., 2nd ed. 1998); 254 pages.

* cited by examiner

*Primary Examiner* — Jonathan S Lau
(74) *Attorney, Agent, or Firm* — Troutman Sanders LLP; John A. Morrissett; Scott A. Bergeson

(57) ABSTRACT

Described herein are stable veterinary formulations and methods of treatment and use, comprising at least one macrocyclic lactone and levamisole as active anthelmintic agents, optionally also with at least one benzimidazole class anthelmintic, wherein the actives are solubilized together in a solvent system comprising dimethylsulfoxide (DMSO). The veterinary formulations, methods and use thereof include the ability to deliver two or more anthelmintic actives in the one solution (or suspension) while also maintaining formulation stability when stored over a period of time. Delivery of different anthelmintics with different activities allows several classes of parasite to be targeted in one dose.

21 Claims, No Drawings

STABLE VETERINARY ANTHELMINTIC FORMULATIONS

CROSS-REFERENCE TO RELATED APPLICATIONS

This application is a Continuation of International Patent Application No. PCT/NZ2015/000018, filed Mar. 24, 2015, which claims priority to New Zealand Patent Application No. 622869, filed Mar. 24, 2014, their entire contents of which are incorporated herein by reference.

TECHNICAL FIELD

Described herein are stable veterinary anthelmintic formulations. More specifically, stable formulations are described comprising at least one macrocyclic lactone and levamisole as active anthelmintic agents, optionally also with at least one benzimidazole class anthelmintic.

BACKGROUND

Diseases caused by parasites result in severe economic losses in farming industry. Traditional veterinary products used to counter internal parasites were typically formulated for oral application—typically sold as drenches. With a need to improve farming efficiency and minimise labour and animal handling, the trend has been for traditional oral drenches to be replaced by products that are topically applied, typically termed 'pour-on' or 'spot-on' products. These products are applied to an animal skin area such as the back of the animal usually as a spray, and the compounds in the product act to transfer the active or actives through the skin and into the animal. Formulating such products requires addressing many issues including:
(a) Keeping the actives in a stable liquid form particularly when stored over time often in trying temperature and moisture conditions;
(b) Having a solution viscosity that is easy to use and which can be applied topically via existing equipment;
(c) Ensuring that most if not all of the active or actives pass through the skin layer as intended; and
(d) Ensuring the active or actives used have the desired efficacy.

Given the varying chemical properties of anthelmintic actives and the relative incompatibility, preparing formulations to achieve the above aims can be challenging, particularly when more than one active is included in a formulation.

Several products are currently available on the market that include macrocyclic lactone anthelmintics for topical application. Many of these use abamectin as the active. Example abamectin based topical products include for example Donaghys ProAbamec™ Pour-On and Baymec™ by Bayer. An alternative is the moxidectin based product sold under the trade name Exodus™ by Merial Ancare.

Several attempts have been made to formulate and commercialise pour-on products that have more than one active ingredient from different chemical classes. The success of these products has been varied and only a small number were successfully commercialised. One example is the product BOSS™ Pour-On for Cattle by Alleva Animal Health Limited, consisting of 1% abamectin and 20% levamisole Base. Another is Combination™ Pour-On for Cattle by Seneca Holdings Limited, consisting of 15% oxfendazole and 10% levamisole Base. Two further examples are Saturn™ Pour-On by Bayer and Eclipse™ Pour-On by Merial Ancare, both consisting of 1% abamectin and 20% levamisole base.

As noted above, formulation challenges exist. The product must remain within specification over the labelled shelf life. In addition macrocyclic lactone and levamisole based products are particularly difficult to formulate together as these two compounds are so chemically incompatible. This incompatibility combined with the higher concentration of levamisole desired for good efficacy renders many common formulation routes unworkable. Other challenges are that the solvent system in pour-on products needs to be non- or low-irritating to the farmer and animal, stable, non-toxic, non-carcinogenic. It is also preferable that a finished product have a viscosity low enough to allow easy dosing yet not so low that the formulation runs off the animal's back or other area to which the formulation is applied. Finally, it is also necessary to achieve full control of parasites and prevent any possible secondary harmful effects, such as causing animal sickness or creating residues in animal meat or milk for human consumption.

Several solvents or combinations of solvents have been described in the art as being suitable for topical transfer of anthelmintic actives.

For example, WO2004/089239 describes a topically applied anthelmintic formulation which comprises at least one macrocyclic lactone and at least one compound selected from praziquantel, morantel and pyrantel. These actives are dissolved in a non-aqueous solvent or solvents mixture that comprises isopropanol, polyethylene glycol, glycerol formal, C8-C10 caprylic/capric triglycerides, diethylene glycol monoethyl ether, propylene glycol monolaureate, dimethylformamide and other compounds.

US2008/0249153 describes an anthelmintic formulation including triclabenzadole in a solution solvent system including at least one solvent selected from 2-pyrrolidone and liquid polyethylene glycol.

WO 2013/043064 discloses a mixture of abamectin and levamisole. However, this mixture degrades rapidly and hence the agents are kept separate (for example, via a two part container) and not mixed until immediately before use.

NZ248486 relates to a stable anthelmintic formulation that comprises a glycol based solvent together with an effective amount of closantel and an effective amount of one or more avermectins or milbemycins. The preferred glycol based solvent contains at least two of water, propylene glycol, polyethylene glycol or glycerol formal.

NZ535644 relates to a pour-on formulation of levamisole base and abamectin, where both actives are dissolved in a solvent system comprising n-methyl-2-pyrrolidone and diethylene glycol n-butyl ether.

NZ336139 describes a veterinary composition comprising at least one ingredient that is lipophilic in character, at least one organic solvent that carries most of lipophilic ingredient, and levamisole dissolved in water.

A similar approach is described in NZ515772 where a macrocyclic lactone, levamisole and benzimidazole are used, where the macrocyclic lactone is dissolved in an organic phase and levamisole and benzimidazole are carried in a pH buffered aqueous system to ensure levamisole stability.

While the above solvents may work, drawbacks exist such as handling issues, potential toxicity issues and the formulations described may lack versatility, for example only being limited to use of levamisole base or salt form and not both forms, or instead only working with one active.

As should be appreciated, while reference has been made above to topically applied formulations, similar formulation issues may exist for delivery via other routes e.g. oral or parenteral routes of administration, and the discussion regarding topical administration above should not be seen as limiting. Further, whilst some products exist, formulations including multiple anthelmintic actives that offer alterative solvent systems may provide alternate advantages or at least may provide the public with a choice.

Further aspects of the formulations, methods and use will become apparent from the ensuing description that is given by way of example only.

SUMMARY

Described herein are stable veterinary formulations comprising at least one macrocyclic lactone and levamisole as active anthelmintic agents, optionally also with at least one benzimidazole class anthelmintic.

In an embodiment, there is provided a veterinary formulation comprising, in solution, a therapeutically effective amount of actives which include at least one macrocyclic lactone anthelmintic compound and levamisole. These actives are solubilised together in a solvent system comprising dimethylsulfoxide (DMSO) and at least one humectant. This veterinary formulation may also include at least one further anthelmintically active compound selected from the benzimidazole class of compounds.

In another embodiment, there is provided a veterinary formulation comprising, in solution, a therapeutically effective amount of the actives which include at least one macrocyclic lactone anthelmintic compound and levamisole. These actives are solubilized together in a solvent system comprising dimethylsulfoxide (DMSO).

In another embodiment, there is provided a stable veterinary formulation comprising 0.5 to 1% by weight of at least one macrocyclic lactone, 10-20% levamisole calculated by weight as levamisole base, and 50-80% dimethylsulfoxide (DMSO).

In another embodiment, there is provided a method of treating internal and/or external parasites in a non-human animal in need thereof by administration of a formulation substantially as described above.

In another embodiment, there is provided a use of the any of the embodiments set forth above in the manufacture of a medicament for the treatment of internal and/or external parasites in an animal in need thereof.

In another embodiment there is provided a use of any of the embodiments set forth above in the treatment of internal and/or external parasites in an animal in need thereof.

The above described formulations, methods and use thereof provide a number of advantages including the ability to deliver two or more anthelmintic actives in the one solution (or suspension) while also maintaining formulation stability when stored over a period of time. Delivery of different anthelmintics with different activities allows several classes of parasite to be targeted in one dose. Either levamisole base or salt may be used. The need for other agents such as stabilisers, buffering agents and surfactants are also minimised or avoided altogether. Further, the formulation viscosity remains at a level that can still easily be administered via traditional equipment such as spray guns, yet is not so low as to run off the animal if applied topically.

DETAILED DESCRIPTION

As noted above, described herein are stable veterinary formulations comprising at least one macrocyclic lactone and levamisole as active anthelmintic agents, optionally also with at least one benzimidazole class anthelmintic.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The term 'treat' or 'treatment' or other grammatical variations thereof in the context of this specification refers to: preventing parasite growth, reduce parasite numbers, killing parasites, killing incoming parasite larvae, lowering the amount of incoming parasite larvae, and combinations thereof.

The term 'solvent system' or grammatical variations thereof refers to a compound or group of compounds in which the anthelmintic agent or agents may dissolve or be suspended.

The term 'solution' or grammatical variations thereof as used herein refers to a liquid substantially absent of any particles therein or a continuous homogenous mixture clearly distinct from formulations/agents that are emulsions, dispersions and specialised micellular formulations.

The term 'non-aqueous' or grammatical variations thereof refers to the formulation contains one or more solvents and is substantially free of or completely free of water.

The term 'suspension' or grammatical variations thereof refers to particles suspended in a liquid solution.

The term 'therapeutically effective amount' or grammatical variations thereof, with reference to an amount or dosage of a composition described herein, refers to an amount of a composition that is sufficient to cause a parasite treatment effect.

The term 'stable' or grammatical variations thereof refers to the concentration of an active agent or agents in the formulation remaining at substantially the same concentration when stored over a time period.

The term 'humectant' or grammatical variations thereof refers to a hygroscopic substance that attracts and retains moisture via absorption.

In a first aspect, there is provided a veterinary formulation comprising, in solution, a therapeutically effective amount of the actives:
 (i) at least one macrocyclic lactone anthelmintic compound; and
 (ii) levamisole;
wherein the actives are solubilised together in a solvent system comprising dimethylsulfoxide (DMSO) and at least one humectant.

The solvent system used in the above formulation may be non-aqueous. In one embodiment, the solvent system has no water present at least at the time of manufacture. Use of a non-aqueous solvent system in the inventor's experience appears to avoid incompatibility issues between macrocyclic lactones and levamisole such as the lipophilic and hydrophilic nature of the actives as well as pH challenges in aqueous solutions.

The formulation may comprise approximately 0.5, or 0.6, or 0.7, or 0.8, or 0.9, or 1.0, or 1.1, or 1.2, or 1.3, or 1.4, or 1.5, or 1.6, or 1.7, or 1.8, or 1.9, or 2.0% by weight of at least one macrocyclic lactone compound. The formulation may comprise approximately 0.5 to 2.0% macrocyclic lactone by weight. In one embodiment, the formulation may comprise approximately 0.5 to 1.0% macrocyclic lactone by weight. The macrocyclic lactone compound may be selected from avermectins, milbemycins, and combinations thereof. The avermectin may be selected from the group consisting of: ivermectin, abamectin doramectin, cydectin, emamectin, selamectin, and combinations thereof. The milbemycin may be moxidectin. In one embodiment, the macrocyclic lactone may be abamectin.

The formulation may comprise approximately 10, or 11, or 12, or 13, or 14, or 15, or 16, or 17, or 18, or 19, or 20, or 21, or 22, or 23, or 24, or 25% levamisole, calculated on levamisole base weight. The formulation may comprise approximately 10 to 25% levamisole, calculated on levamisole base weight. In one embodiment, the formulation may comprise approximately 10-20% levamisole, calculated on levamisole base weight. The levamisole may be either in base or in an ionic form. The ionic form may be a hydrochloride salt form. The inventor has found that is may be possible to use either form unlike most other products that require one form or the other. This allows the formulation described herein to be more versatile than many art products as either form of levamisole may be used without an impact on stability or efficacy.

Dimethylsulfoxide (also referred herein as DMSO) may be present in the formulation at a concentration of approximately 50, or 55, or 60, or 65, or 70, or 75, or 80% by weight. DMSO may be present at a concentration of approximately 50 to 80% by weight. In one embodiment, DMSO may be present at a concentration of 60 to 70% by weight.

DMSO is a naturally occurring chemical found in many products including vegetables, fruits, grains and animal products. Therapeutic interest began in 1963, when DMSO was reported to penetrate through skin and produce analgesia, decrease pain and promote tissue healing. In human medicine, DMSO is used topically to decrease pain and speed of healing of wounds, burns and muscle and skeletal injuries. It is also used topically to treat or address the symptoms of conditions such as headaches, inflammation, rheumatoid arthritis, cataracts and glaucoma. DMSO may also be used intravenously to treat bladder infections and chronic inflammatory bladder disease.

The U.S. Food and Drug Administration (FDA) have approved certain DMSO products for placement inside the bladder to treat symptoms of chronic inflammatory bladder disease. DMSO is also used as a solvent for herbicides, fungicides, antibiotics and plant hormones. According to American Chemical Society (Annual Meeting, Aug. 20-24, 2000, Washington D.C.) one of the most significant properties of DMSO is it low toxicity. The EPA describes DMSO as being environmentally compatible classified it as "practically non toxic".

The acute oral toxicity of DMSO in terms of LD50 literature averages for three animal species, were converted to human equivalent in pounds with a safety factor is 10 for interspecies extrapolation and other testing uncertainties.

Two conclusions can be drawn: the human oral dose of DMSO required to kill 50% of those ingesting it (LD50) is fairly high; and DMSO is approximately 5 times safer than N-methylpyrrolidone, which is one of the main solvents used in other above described and commercialised anthelmintic topical formulations.

Expressed another way, use of DMSO in veterinary formulations may be safer to use on animals and for human handling than existing formulations using other solvents used in anthelmintic formulations. DMSO therefore presents as a very useful alternative solvent for both animal administration and human handling however, use in anthelmintic topical delivery has not to the inventor's knowledge been explored.

Based on the inventor's work, several unexpected benefits resulted from using DMSO for anthelmintic compounds that were not apparent until tested by the inventor.

One unexpected finding was that DMSO allows multiple anthelmintic compounds from different classes of activity and often incompatible to be solubilised together and avoids problems often associated with such mixtures. Specifically, the inventor found formulations could be produced from a mix of at least macrocyclic lactones and levamisole.

It was also unexpectedly found that the solvent system described above allows use of levamisole base or salt form, for example hydrochloride form, without impacting the final product stability or efficacy. Prior art tends to lead away from such ease of compatibility where a particular chemical form (base or salt) may be required in order to provide a stable formulation for a prolonged period of time, particularly where buffering agents or stabilising agents are used.

With respect to stability, formulations produced were tested by the inventor and found to remain stable for prolonged periods of time in trying temperatures and humidities. The inventor found that the formulation may be stable at accelerated ageing conditions of 54° C. and 50% humidity for at least two weeks. This result was unexpected since art teaches of compatibility issues between different classes of anthelmintic agents and levamisole in particular is prone to reduce in concentration when in moist conditions. Further, DMSO does not present as a solvent that necessarily would have the improved stability found. One possibility for the unexpected stability noted may be the fact that DMSO is highly hygroscopic and is able to absorb up to 30% of moisture hence the formulation as a whole appears to be more resilient to exposure to moisture.

As noted above, the formulation may also include at least one humectant. The humectant or humectants chosen may be selected on also having solvent properties and being physiologically acceptable with animal skin. The humectant or humectants may be added to volume 100%. In selected embodiments, the humectant or humectants may be added at a concentration of approximately 5, or 6, or 7, or 8, or 9, 10, or 11, or 12, or 13, or 14, or 15, or 16, or 17, or 18, or 19, or 20% by weight. The choice of humectant or humectant used may be in part governed by their effectiveness but also by their safety for handling as well as for the animal to which the formulation is applied. Generally recognised as safe (GRAS) approved humectant may be particularly useful. In selected embodiments, the at least one humectant may be selected from: propylene glycol, hexylene glycol, butylene glycol, at least one sugar alcohol compound, and combinations thereof. The sugar alcohol may be selected from: glycerine, sorbitol, xylitol, maltitol, and combinations thereof. In selected embodiments, the at least one humectant may be a mixture of propylene glycol and either sorbitol or glycerine at a ratio (propylene glycol to sorbitol/glycerine) of approximately 10:1 to 6:1 w/w. In one embodiment, the humectant may be propylene glycol. Propylene glycol has a variety of useful properties in the context of the described formulation beyond just humectant properties including acting as solvent, acting as a preservative and being GRAS approved. Such a humectant may also have emollient properties as well. In addition, such humectants may assist by preventing skin dryness at the site of administration.

The formulation may also include at least one further anthelmintically active compound selected from the benzimidazole class of compounds. Where present, the benzimidazole compound or compounds may be present at a concentration of approximately 4, or 5, or 6, or 7, or 8, or 9, or 10, or 11, or 12, or 13, or 14, or 15, or 16, or 17, or 18, or 19, or 20% by weight. The benzimidazole may be present at a concentration of approximately 4 to 20%. In one embodiment, the formulation may include approximately 15% benzimidazole by weight. Examples of such actives may include: albendazole, oxfendazole, fenbendazole, mebendazole, thiabendazole, triclabendazole, flubendazole, and combinations thereof. It is the inventor's experience that when a benzimidazole or benzimidazoles are added to the above solution, the formulation becomes a suspension (non-aqueous). The inventor has found that benzimidazoles, often incompatible in formulation with other actives, can in this instance be placed in suspension with the other solubilised actives. Further, the benzimidazole compound or compounds do not impact on product stability and, on administration, deliver an efficacious dose to the animal without leaving residues in the meat or milk from the animal. The inventor found that unlike many art formulations, benzimidazoles may be directly added to the levamisole and macrocyclic lactone solution thereby forming a suspension without altering the formulation stability or other handling characteristics. The presence of DMSO may be helpful in making the benzimidazole compound(s) compatible. DMSO in the inventor's experience also serves as an effective carrier for benzimidazole anthelmintics, promoting their percutaneous absorption in therapeutically effective concentrations required to provide control internal parasites.

Where one or more benzimidazole compounds are included, the formulation may further comprise one or more dispersing and/or suspending agents. By way of example, bentonite may be used as a dispersing/suspending agent. Other compounds that may be used include glycerol palmistearate, xanthan gum and colloidal silica. Where a dispersing/suspending agent is used. The concentration may be approximately 0.1%.

The product may include other medicaments or other supplements that are soluble in the solvent system. The medicaments or supplements may include substances such as anthelmintics, vitamins, antigens, vaccines, trace minerals and/or vitamin supplements and other substances that may be useful for promoting the health of the animal. The minerals if used may be selected from one or more sources of: cobalt, copper, iodine, selenium and zinc. The observed compatibility also extends to using other agents and, as may be appreciated, administering multiple actives in one dose may be useful for example to reduce labour by administering one dose rather than several doses.

Further compounds such as buffering agents, stabilisers and preservatives may optionally be added however, in the inventor's experience, these are not essential. It was also surprisingly found that use of DMSO as a part of the solvent system significantly decreases the finished product cost. This is because DMSO appears to remove or at least significantly reduce the need for further compounds typically used in art formulations including (but not limited to): buffering agents, stabilisers and preservatives. In the inventor's experience, it is possible to manufacture formulations as described above without using buffering agents, stabilisers and preservatives and still have very acceptable stability and efficacy properties. Where used, the buffering agents, stabilisers and preservatives are present at a concentration of approximately 0.1, or 0.5, or 1.0, or 1.5, or 2.0% of the formulation by weight. The concentration may be 0.1 to 2.0% by weight.

Whilst not essential, the product may further include one or more excipients. Examples of excipients that may be added include dyes, preservatives, thickeners and buffers.

A further advantage of the formulation is that the viscosity remains at a level that is sufficiently low to allow absorption of the actives on administration plus use in existing application equipment. Further, the viscosity is not so low that the formulation runs off the application area. The anticipated viscosity of the formulation is likely to be subject to wide variation as the formulation components may influence viscosity and also, environmental temperatures may also influence viscosity. In one embodiment, the viscosity may be approximately 1.0, or 2.5, or 5.0, or 7.5, or 10, or 25, or 50, or 75, or 100, or 150, or 200, or 250, or 300, or 350, or 400, or 450, or 500, or 550, or 600, or 650, or 700, or 750, or 800, or 850, or 900, or 950, or 1000, or 1250, or 1500, or 1750, or 2000, or 2250, or 2500, or 2750, or 3000, or 3200 cP. In one embodiment, the viscosity may range from 1.0 to 3200 cP. In one embodiment the viscosity may range from 250 to 2500 cP. The inventor has found that the formulation described herein is easy to handle such as when pouring the formulation (pour-on trans-dermal delivery) or when delivering in spot form. A lower viscosity and low shear rate means easier mixing for less energy input during manufacture and less force being required to administer the formulation and more accurate measuring of required dose. Having to exert large amounts of energy in order to mix the formulation or pour/spot on administration may not be ideal as, besides added labour or energy costs, mixing may not be as complete as desired. A lower viscosity particularly at low energy inputs may be useful.

The formulation may further include 0.25, or 0.5, or 0.75, or 1.0, or 1.25, or 1.5% by weight of at least one surfactant and/or wetting agent. The surfactant/wetting agent may be present at a concentration from 0.25 to 1.5% by weight. In one embodiment, the surfactant/wetting agent may be present at a concentration from 0.25 to 1.0%. Examples of surfactant/wetting agents that may be used include Tween 80 and/or EO/PO block copolymers.

In a second aspect, there is provided a veterinary formulation comprising, in solution, a therapeutically effective amount of the actives:
  (i) at least one macrocyclic lactone anthelmintic compound; and
  (ii) levamisole;
wherein the actives are solubilised together in a solvent system comprising dimethylsulfoxide (DMSO).

In a third aspect, there is provided a stable veterinary formulation in the form of a solution comprising:
  (a) 0.5 to 1% by weight of at least one macrocyclic lactone;
  (b) 10-20% levamisole calculated by weight as levamisole base; and
  (c) 50-80% dimethylsulfoxide;
As noted above, the formulations may further include in suspension, at least one benzimidazole class anthelmintic.

The example formulations below are particularly suitable for topical/trans-dermal administration. This is because they present is either a low viscosity solution or suspension with sufficient transdermal penetration that they are able to pass through the derma layer. In one embodiment, the above formulations may be sold as a pour-on or spot-on product for administration to the skin and fur or hair of an animal. Despite the above, the formulations described may also be administered orally or parenterally and the above description regarding topical application should not be seen as limiting.

The above dosage rates for the active compounds are based broadly on application rate per kg of live weight of animal. The aim is to treat the animal which, as defined herein refers to: preventing parasite growth, reduce parasite numbers, killing parasites, killing incoming parasite larvae, lowering the amount of incoming parasite larvae, and combinations thereof. As should be appreciated, the dose rate may vary depending on many factors such as animal species, animal metabolism, specific animal factors such as existing parasite loading versus prevention etc. Given the above wide variation in potential doses, the above concentrations of active included should not be seen as limiting and other rates or doses may be used.

In a fourth aspect, there is provided a method of treating internal and/or external parasites in a non-human animal in need thereof by administration of a formulation substantially as described above.

In a fifth aspect, there is provided the use of a formulation substantially as described above in the manufacture of a medicament for the treatment of internal and/or external parasites in an animal in need thereof.

In a sixth aspect there is provided a formulation substantially as described above for use in the treatment of internal and/or external parasites in an animal in need thereof.

The parasites to which the formulation may be anthelmintically active include endo and ecto parasites. In one embodiment, the parasites treated may include: *Haemonconchus* spp., *Ostertagia* spp., *Trichostrongylus* spp., *Coopera* spp., *Nematodirus* spp. *Chabertia* spp., *Oesophagostomum* spp., *Trichuris* spp., *Strongyloides* spp., *Bunostomum* spp., *Oestrus* spp., *Dictycaulus* spp., *Fasciola* spp. and *Monezia* spp.

The animal may be a non-human animal. The animal may of bovine, ovine, cervine, porcine, canine or feline genus. The animal may be a dairy cow, steer, calf, sheep or lamb. This list should not however be seen as limiting as the formulation may be effective for a variety of animals.

The kinetics of the dose irrespective of route of administration, may, once administrated, be equivalent to that of oral drench formulations with an initial spike in anthelmintic concentration in the blood stream of the animal lasting for up to 24 hours followed by a gradual decline in concentration over time. It is anticipated that all trace of the anthelmintic will have gone within at most two weeks post administration.

The above formulations and methods and use thereof provide a number of advantages including the ability to deliver two or more anthelmintic actives in the one solution (or suspension) whilst also maintaining formulation stability when stored over a period of time. Delivery of different anthelmintics with different activities allows several classes of parasite to be targeted in one dose. Either levamisole base or salt may be used. The need for other agents such as stabilisers, buffering agents and surfactants are also minimised or avoided altogether. Further, the formulation viscosity remains at a level that can still easily be administered via traditional equipment such as spray guns, yet is not so low as to run off the animal if applied topically.

The embodiments described above may also be said broadly to consist in the parts, elements and features referred to or indicated in the specification of the application, individually or collectively, and any or all combinations of any two or more said parts, elements or features.

Further, where specific integers are mentioned herein which have known equivalents in the art to which this invention relates, such known equivalents are deemed to be incorporated herein as of individually set forth.

WORKING EXAMPLES

The above described formulations, methods and uses are now described by reference to specific examples.

Example 1

Example formulations are described for use as pour-on trans-dermal products.

| Formulation/Feature/Compound | Formulation | | | | | | |
|---|---|---|---|---|---|---|---|
| | 1 | 2 | 3 | 4 | 5 | 6 | 7 |
| Application Rate | 1 ml per 20 kg live weight | 1 ml per 20 kg live weight | 1 ml per 20 kg live weight | 1 ml per 10 kg live weight | 1 ml per 10 kg live weight | 1 ml per 10 kg live weight | 1 ml per 20 kg live weight |
| Abamectin | 1% | — | 1% | 0.5% | 0.5% | 0.5% | 1% |
| Ivermectin | — | 1% | — | — | — | — | — |
| Levamisole Base | 20% | 20% | — | 10% | — | — | 20% |
| Levamisole HCL | — | — | 21% | — | 10.5% | 10.5% | — |
| Albendazole | — | — | — | 15% | — | — | — |
| Oxfendazole | — | — | — | — | 15% | — | — |
| Fenbendazole | — | — | — | — | — | 15% | — |
| DMSO | 60% | 60% | 70% | 60% | 65% | 65% | 60% |
| EO/PO Block co-polymer | 0.5% | 0.25% | — | — | 1% | 1% | 0.5% |
| Sorbitol | — | 10% | — | — | — | — | To volume, 100% |
| Tween 80 | — | — | 0.75% | 0.5% | — | — | — |

-continued

| Formulation/Feature/Compound | Formulation | | | | | | |
|---|---|---|---|---|---|---|---|
| | 1 | 2 | 3 | 4 | 5 | 6 | 7 |
| Bentonite | — | — | — | 0.1% | 0.1% | 0.1% | — |
| Vitamin E | — | — | — | — | 5% | — | — |
| Propylene glycol | To volume, 100% | To volume, 100% | To volume, 100% | To volume, 100% | To volume, 100% | To volume, 100% | — |

Example 2

An experiment was completed to confirm the formulation stability.

Two samples were prepared and tested to confirm stability when subjected to high moisture conditions and elevated temperatures for prolonged periods of time.

The representative samples were formulation 1 in Example 1 (Sample 1) above and, as a reference formulation, a second comparison sample was produced using a more traditional solvent where the same ingredients were used except that DMSO was substituted with 2-pyrrolidone (Sample 2).

Samples were stored at 54° C. at humidity of 50% for 14 days. As may be appreciated, this represents very challenging conditions and is a clear representation of accelerated ageing.

It was found that Sample 1 did not undergo significant degradation. The formulation remained as a solution and the concentrations of both active ingredients (abamectin and levamisole) decreased by only 0.25% for abamectin and 1% for levamisole calculated based on the initial active ingredient concentration. This is within allowable label variation and an appreciable difference in efficacy would not be expected by this change. By comparison, Sample 2 was less stable, with levamisole decreasing in concentration by 3.5% calculated on initial concentration which is to a point that is less acceptable. Abamectin did not show a significant change for Sample 2, only decreasing by 0.24% of the initial concentration.

Based on the above comparison, the above described formulations containing DMSO are stable and, at least in respect of levamisole, the formulations described may also provide a superior stability over art formulations.

Aspects of the formulations, methods and uses have been described by way of example only and it should be appreciated that modifications and additions may be made thereto without departing from the scope of the claims herein.

I claim:

1. A veterinary formulation comprising, in solution, a therapeutically effective amount of the actives:
   (i) at least one macrocyclic lactone anthelmintic compound; and
   (ii) levamisole;
   wherein the actives are solubilised together in a solvent system comprising dimethylsulfoxide (DMSO) and at least one humectant; and
   wherein the formulation is a topical formulation and a single dosage form.

2. The formulation of claim 1, wherein the solvent system is non-aqueous.

3. The formulation of claim 1, wherein the macrocyclic lactone is included at a concentration of approximately 0.5 to approximately 2.0% by weight.

4. The formulation of claim 1, wherein the macrocyclic lactone compound is selected from the group consisting of: ivermectin, abamectin doramectin, cydectin, emamectin, selamectin, and moxidectin, and combinations thereof.

5. The formulation of claim 1, wherein the levamisole is included at a concentration of approximately 10 to approximately 25% levamisole, calculated on levamisole base weight.

6. The formulation of claim 1, wherein the levamisole is levamisole base or levamisole hydrochloride salt.

7. The formulation of claim 1, wherein the at least one humectant is added to volume or 100% by weight.

8. The formulation of claim 1, wherein the at least one humectant comprises one or more compounds of: propylene glycol, hexylene glycol, butylene glycol, and at least one sugar alcohol compound.

9. The formulation of claim 8, wherein the at least one humectant is a mixture of propylene glycol and either sorbitol or glycerine at a ratio (propylene glycol to sorbitol/glycerine) of approximately 10:1 to approximately 6:1 w/w.

10. The formulation of claim 1, wherein the formulation includes at least one additional anthelmintically active compound selected from a benzimidazole class of compounds.

11. The formulation of claim 10, wherein the benzimidazole compound or compounds are included at a concentration of approximately 4 to approximately 20% by weight.

12. The formulation of claim 10, wherein the benzimidazole compound or compounds are selected from the group consisting of: albendazole, oxfendazole, fenbendazole, mebendazole, thiabendazole, triclabendazole, and flubendazole.

13. The formulation of claim 9, wherein the formulation also includes at least one dispersing and suspending agent.

14. The formulation of claim 1, wherein the formulation includes at least one further medicament or other supplement that is soluble in the solvent system.

15. The formulation of claim 1, wherein the formulation includes at least one additional agent selected from a buffering agent, stabilizer, and a preservative.

16. The formulation of claim 15, wherein each of the at least one additional agent is included at a concentration of approximately 0.1 to approximately 2.0% by weight.

17. The formulation of claim 1, wherein the formulation includes one or more excipients selected from: dyes, preservatives, thickeners, buffers, and combinations thereof.

18. The formulation of claim 1, wherein the formulation has a viscosity of approximately 1.0 to approximately 3200 cP.

19. The formulation of claim 1, wherein the formulation further includes at least one surfactant and/or wetting agent.

20. The formulation of claim 1, wherein the active concentration remains within approximately 0.25% of the starting concentration when stored at 54° C. and 50% humidity for two weeks.

21. A method of treating internal and/or external parasites in a non-human animal in need thereof comprising administering the formulation of claim 1.

* * * * *